(12) United States Patent
Heacock et al.

(10) Patent No.: US 9,486,591 B2
(45) Date of Patent: *Nov. 8, 2016

(54) COLOR CHANGEABLE DYES FOR INDICATING EXPOSURE, METHODS OF MAKING AND USING SUCH DYES AND APPARATUSES INCORPORATING SUCH DYES

(71) Applicant: Sensor International, LLC, Maple Valley, WA (US)

(72) Inventors: Gregory Lee Heacock, Maple Valley, WA (US); Dion Arledge Rivera, Ellensburg, WA (US)

(73) Assignee: Sensor International, LLC, Maple Valley, WA (US)

( * ) Notice: Subject to any disclaimer, the term of this patent is extended or adjusted under 35 U.S.C. 154(b) by 63 days.

This patent is subject to a terminal disclaimer.

(21) Appl. No.: 14/161,127

(22) Filed: Jan. 22, 2014

(65) Prior Publication Data

US 2014/0134443 A1    May 15, 2014

Related U.S. Application Data

(63) Continuation of application No. 11/315,840, filed on Dec. 9, 2011, now Pat. No. 8,663,998.

(51) Int. Cl.
*A61M 5/50* (2006.01)
*A61B 17/3211* (2006.01)
(Continued)

(52) U.S. Cl.
CPC ............. *A61M 5/50* (2013.01); *A61B 17/3211* (2013.01); *A61B 90/92* (2016.02); *C09K 9/02* (2013.01);
(Continued)

(58) Field of Classification Search
CPC   A61M 5/50; A61M 2205/6081; G02B 1/10; G02C 7/02; A61B 17/3211; A61B 2019/444; A61B 2019/4852; A61B 2019/4873
USPC .......... 503/202; 604/111; 606/181; 436/2, 8, 436/55, 166, 2.8; 252/408.1; 351/159.28
See application file for complete search history.

(56) References Cited

U.S. PATENT DOCUMENTS

| 2,768,976 A | 10/1973 | Hu |
| 3,899,295 A | 8/1975 | Halpern |

(Continued)

FOREIGN PATENT DOCUMENTS

| CN | 101479584 | 7/2009 |
| CN | 101501468 | 8/2009 |

(Continued)

OTHER PUBLICATIONS

PCT, Notification Concerning Transmittal of International Preliminary Report on Patentability, in International application No. PCT/US2012/063797, dated Jun. 19, 2014 (10 pages).

(Continued)

*Primary Examiner* — Bruce H Hess
(74) *Attorney, Agent, or Firm* — McAndrews, Held and Malloy

(57) ABSTRACT

According to embodiments of the present application, a color changeable dye can comprise a redox indicator, a reduction reaction initiator, an electron donor, an oxygen scavenger, an indicator barrier agent, a thickening agent and an agent to facilitate mixing. The color changeable dye is a first color in the presence of oxygen, capable of changing to a second color upon reduction in a substantially oxygen free environment, and capable of changing back to the first color after exposure to oxygen for a period of time corresponding to the intended use time of a disposable or limited use product. Methods of making and using the color changeable dye and apparatuses incorporating such dye are also disclosed.

20 Claims, 16 Drawing Sheets
(11 of 16 Drawing Sheet(s) Filed in Color)

(51) Int. Cl.
*G02B 1/10* (2015.01)
*G02C 7/02* (2006.01)
*C09K 9/02* (2006.01)
*A61B 19/00* (2006.01)
*B44F 1/10* (2006.01)

(52) U.S. Cl.
CPC . *G02B 1/10* (2013.01); *G02C 7/02* (2013.01);
*A61B 2019/4852* (2013.01); *A61B 2019/4873* (2013.01); *A61B 2090/0804* (2016.02); *A61B 2090/0814* (2016.02); *A61M 2205/6081* (2013.01); *B44F 1/10* (2013.01); *C09K 2211/1029* (2013.01); *Y10T 436/10* (2015.01); *Y10T 436/12* (2015.01)

(56) References Cited

U.S. PATENT DOCUMENTS

| | | | |
|---|---|---|---|
| 4,003,709 | A | 1/1977 | Eaton |
| 4,098,577 | A | 7/1978 | Halpern |
| 4,526,752 | A | 7/1985 | Perlman et al. |
| 5,159,360 | A | 10/1992 | Stoy et al. |
| 5,942,438 | A | 8/1999 | Antonoplos et al. |
| 6,060,210 | A | 5/2000 | Eda et al. |
| 6,114,509 | A | 9/2000 | Olsen et al. |
| 6,132,086 | A | 10/2000 | Henwood |
| 6,218,189 | B1 | 4/2001 | Antonoplos et al. |
| 6,518,231 | B2 | 2/2003 | Appel et al. |
| 6,634,747 | B1 | 10/2003 | Atkins et al. |
| 6,790,411 | B1 | 9/2004 | Read |
| 6,851,808 | B2 | 2/2005 | Heacock |
| 7,219,799 | B2 | 5/2007 | Bonnette et al. |
| 7,244,252 | B2 | 7/2007 | Berndt |
| 7,785,299 | B2 | 8/2010 | Crawford et al. |
| 8,137,303 | B2 | 3/2012 | Crawford et al. |
| 8,163,237 | B2 | 4/2012 | Crawford et al. |
| 8,257,663 | B2 | 9/2012 | Crawford et al. |
| 8,338,131 | B2 * | 12/2012 | Callen ............... C12N 9/2417 435/183 |
| 8,388,131 | B2 | 3/2013 | Heacock |
| 8,663,998 | B2 | 3/2014 | Heacock |
| 2002/0023642 | A1 | 2/2002 | Allard et al. |
| 2002/0137123 | A1 | 9/2002 | Hui |
| 2004/0180391 | A1 | 9/2004 | Gratzl et al. |
| 2005/0041200 | A1 | 2/2005 | Rich |
| 2005/0164898 | A1 | 7/2005 | Kasturi et al. |
| 2006/0046301 | A1 | 3/2006 | Happe |
| 2006/0054525 | A1 | 3/2006 | Dean et al. |
| 2006/0054526 | A1 | 3/2006 | Dean |
| 2006/0069305 | A1 | 3/2006 | Couvillon et al. |
| 2006/0110835 | A1 | 5/2006 | Gohil |
| 2006/0181676 | A1 | 8/2006 | Tucker et al. |
| 2007/0017042 | A1 | 1/2007 | Cincotta et al. |
| 2007/0140911 | A1 | 6/2007 | Carney et al. |
| 2008/0129960 | A1 | 6/2008 | Heacock |
| 2009/0301382 | A1 | 12/2009 | Patel |
| 2009/0303440 | A1 | 12/2009 | Heacock et al. |
| 2010/0112680 | A1 | 5/2010 | Brockwell et al. |
| 2011/0130727 | A1 | 6/2011 | Crawford et al. |
| 2011/0130728 | A1 | 6/2011 | McKinnon et al. |
| 2011/0259086 | A1 * | 10/2011 | Harris ............... G01M 3/042 73/40.7 |
| 2013/0130399 | A1 | 5/2013 | Mills |
| 2013/0150785 | A1 | 6/2013 | Heacock |
| 2013/0269592 | A1 | 10/2013 | Heacock et al. |
| 2015/0087076 | A1 | 3/2015 | Heacock |

FOREIGN PATENT DOCUMENTS

| | | |
|---|---|---|
| EP | 0 231 499 A1 | 8/1987 |
| EP | 2021755 | 5/2007 |
| EP | 2383559 A1 | 11/2011 |
| JP | 2004-045365 | 2/2004 |
| JP | 2004-323740 | 11/2004 |
| JP | 2007-183125 | 7/2007 |
| WO | 2003/070139 A2 | 8/2003 |
| WO | WO 02/099416 | 3/2006 |
| WO | 2006/058228 A1 | 6/2006 |
| WO | 2007/018301 A1 | 2/2007 |
| WO | WO 2008-067143 * | 6/2008 ............... A61B 3/00 |
| WO | 2013085655 | 6/2013 |

OTHER PUBLICATIONS

Ex Parte Quayle Action in U.S. Appl. No. 12/504,107, filed Oct. 16, 2012.
Extended Supplementary European Search Report, EP Application No. EP07864168, Mar. 1, 2011.
Final Rejection in U.S. Appl. No. 11/607,298, filed Jan. 26, 2009.
International Search Report and Written Opinion of the International Searching Authority, or the Declaration, in International application No. PCT/US2012/63797, dated Jan. 17, 2013. (10 pages).
International Search Report corresponding to International Application No. PCT/US2007/84186, mailed Sep. 2, 2008, 2 pages.
Issue Notification in U.S. Appl. No. 12/504,107, filed Feb. 13, 2013.
Michael Freemantle, Intelligence Ink Detects Oxygen, Chemical Gas Sensing, Aug. 2, 2004, p. 11, vol. 82, No. 31, Chemical & Engineering News USA.
Non-Final Rejection in U.S. Appl. No. 11/607,298, filed Jul. 29, 2008.
Non-Final Rejection in U.S. Appl. No. 12/504,107, filed Mar. 28, 2012.
Non-Final Rejection in U.S. Appl. No. 13/315,840, filed Nov. 8, 2013.
Notice of Allowance in U.S. Appl. No. 12/504,107, filed Nov. 19, 2012.
Notification Concerning Transmittal of International Preliminary Report on Patentability, PCT/US2007/084186, mailed Jun. 11, 2009, 12 pages.
Requirement for Restriction/Election in U.S. Appl. No. 11/607,298, filed Mar. 18, 2008.
Requirement for Restriction/Election in U.S. Appl. No. 12/504,107, filed Oct. 26, 2011.
Requirement for Restriction/Election in U.S. Appl. No. 13/315,840, filed Sep. 12, 2013.
Swann et al., "Designing Out Curative Syringe Reuse: Maximising Global Acceptance and Impact by Design," Internet Citation, http://eprints.hud.ac.uk/11783/ [dated Sep. 18, 2013] abstract.
The Guardian, Architecture and Design Blog with Oliver Wainwright, "How colour-changing technology could revolutionise the medical industry," Internet Citation, http://www.theguardian.cco/artanddesign/architectarc-design-blog/2013/aug/28/colour-changing-syringe-medical-design [dated Sep. 18, 2013].
Written Opinion of the International Searching Authority corresponding to International Application Serial No. PCT/US2007/84186, mailed Sep. 2, 2008, 12 pages.
European Patent Office, Communication with extended European search report, in Application No. 14166858.2, dated Sep. 4, 2014 (7 pages).
European Patent Office, Communication with extended European search report in application No. 12855085.2, dated Aug. 3, 2015 (6 pages).
PCT, Notification of Transmittal of the International Search Report and the Written Opinion of the International Searching Authority, in Application No. PCT/US2015/032885, dated Aug. 14, 2015 (10 pages).
PCT, Notification of Transmittal of the International Search Report and the Writen Opinion of the International Searching Authority, or the Declaration, in Application No. PCT/US14/57225, dated Dec. 17, 2014 (11 pages).
PCT, Written Opinion of the International Searching Authority, Application No. PCT/US2014/057225, dated Sep. 24, 2014, 4 pages.
PCT, International Search Report, Application No. PCT/US2014/057225, dated Sep. 24, 2014, 2 pages.

(56) References Cited

OTHER PUBLICATIONS

PCT, Written Opinion of the International Searching Authority, Application No. PCT/US2015/032885, dated May 28, 2015, 5 pages.

PCT, International Search Report, Application No. PCT/US2015/032885, dated May 28, 2015, 2 pages.

Japanese Patent Office, Office action in patent application No. 2014-545905 dated May 17, 2016. (12 pages, including x English translation).

* cited by examiner

COLOR CHANGEABLE DYES FOR INDICATING EXPOSURE, METHODS OF MAKING AND USING SUCH DYES AND APPARATUSES INCORPORATING SUCH DYES

RELATED APPLICATIONS

This application claims priority to and is a continuation of U.S. patent application Ser. No. 13/315,840 having a filing date of Apr. 23, 2012, which is incorporated herein by reference in its entirety.

BACKGROUND OF THE APPLICATION

Generally speaking, the present application relates to a color changeable dye that changes color after being exposed to oxygen for a predetermined period of time. The color changeable dye is intended for use on disposable, limited or restricted use products that can transmit contaminants, and disease to a person or cause infection if reused or used beyond a recommended period of time. The color changeable dye acts to indicate that the product should no longer be used. The present application also relates to methods of making and using the color changeable dye and apparatuses incorporating the color changeable dye.

Many products currently marketed and sold to consumers are designed for limited use. These products are usually associated with a single event, a restricted time period or restricted access. There are many reasons for the need of single use or limited use products.

There are numerous examples of single use products in the medical field. One example is a disposable syringe. Instrument contamination and cross infection between patients is an ever present concern if the syringe is inadvertently reused. It is a particular concern in some countries where repeated use of instruments is known to transmit serious diseases such as HIV and hepatitis. Medical and ophthalmic devices that must be sterilized such as scalpels or tonometers (e.g., for the measurement of a patient's intraocular pressure) body piercing and tattooing instruments used on multiple clients also give cause for concern. Needles used in acupuncture offer another example. Decontamination procedures or employment of single-use devices are methods used to control cross infection, but they rely on personnel awareness, willingness to follow protocol, monitoring and documentation.

The limited use type of product is usually associated with goods that should be used for a restricted time period. One example of this type of product is "daily wear" or disposable contact lenses. Contact lenses for refractive correction or cosmetic purposes require suitable wear and care regimes in order to maintain good eye health. Non-compliance on the part of the patient, either through choice or due to lack of education, can injure the eye. Frequent replacement lenses are sometimes worn for longer than recommended or they may be stored or cleaned inappropriately.

U.S. Pub. No. 2009/0303440, which is co-owned by applicant and incorporated herein in its entirety by reference, previously addressed a similar problem. U.S. Pub. No. 2009/0303440 presented a disposable limited or restricted use apparatus that includes a color changeable portion wherein the time that the color change occurs is controlled so that it coincides to the approximate time of the end of one use of a single use apparatus or to the approximate expiration time for extended but limited or restricted use apparatus.

The present application provides the additional benefit of allowing the color changeable dye to be applied to a disposable limited or restricted use apparatus in the presence of oxygen in its oxidized state in a first color. It can then later be reduced after the disposable limited or restricted use apparatus has been packaged in a substantially oxygen free environment to its reduced state in a second color. This allows the color changeable dye of the present application to be applied in the presence of oxygen rather than in a substantially oxygen free argon environment.

BRIEF SUMMARY OF THE APPLICATION

The present application relates to a color changeable dye that changes color after being exposed to oxygen for a predetermined period of time. The color changeable dye is intended for use on disposable, limited or restricted use products that can transmit contaminants, and disease to a person or cause infection if reused or used beyond a recommended period of time. The color changeable dye acts to indicate that the product should no longer be used. The present application also relates to methods of making and using the color changeable dye and apparatuses incorporating the color changeable dye.

According to embodiments of the present application, a color changeable dye can comprise a redox indicator, a reduction reaction initiator, an electron donor, an oxygen scavenger, an indicator barrier agent, a thickening agent and an agent to facilitate mixing. The color changeable dye is a first color in the presence of oxygen, capable of changing to a second color upon reduction in a substantially oxygen free environment, and capable of changing back to the first color after exposure to oxygen for a period of time corresponding to the intended use time of a disposable or limited use product.

The redox indicator of the color changeable dye may be indigo-tetrasulfonate in which case the first color may be blue and said second color may be translucent or water white. The reduction reaction initiator of the color changeable dye may be titanium dioxide and the reduction of the color changeable dye may be initiated using UV light. The electron donor of the color changeable dye may be glycerol. The oxygen scavenger of the color changeable dye may be sodium bisulfate and/or ascorbic acid. The indicator barrier agent of the color changeable dye may be poly(diallyldimethylammonium chloride). The thickening agent of the color changeable dye may be 2-hydroxyethyl cellulose. The agent to facilitate mixing of the color changeable dye may be bentonite nanoclay. In the color changeable dye of the present application the period of time may be a matter of minutes, i.e. less than approximately 60 minutes, or a matter of hours, i.e. between about 1 and about 168 hours or longer or shorter as the application requires.

According to embodiments of the present application, a disposable ophthalmic or medical apparatus comprises a disposable ophthalmic or medical device having a portion that comes in contact with, e.g., bodily fluids or tissue so as to be susceptible to the transmission of contaminates or disease to a patient and a color changeable dye disposed on the device wherein said color changeable dye is a first color in the presence of oxygen, capable of changing to a second color upon reduction in a substantially oxygen free environment, and capable of changing back to the first color after exposure to oxygen for a period of time corresponding to the intended use time of said disposable ophthalmic or medical device.

The ophthalmic or medical apparatus could be, e.g., a disposable contact lens, a disposable scalpel, a disposable a syringe and/or a disposable ophthalmic lens through which a clinician looks to view a patients' eye.

According to another embodiment of the present application, an apparatus with time controlled color change indication comprises a limited use apparatus that has a portion that comes in contact with bodily fluids or tissue and can potentially cause harm to a person if used beyond a limited time or reused and a color changeable dye disposed directly on a portion of the apparatus wherein said color changeable dye is a first color in the presence of oxygen, capable of changing to a second color upon reduction in a substantially oxygen free environment, and capable of changing back to the first color after exposure to oxygen for a period of time corresponding to a defined time indicating that the apparatus is no longer to be used.

The apparatus could be a cosmetic applicator or an oral medication or pill having an expiration date after which said apparatus should not be used.

According to another embodiment of the present application a method of producing a color changeable dye can comprise: dissolving a redox indicator and a thickening agent in an aqueous solvent to form a stock solution; providing a reduction reaction initiator; adding an indicator barrier agent to said reduction reaction initiator to form a solution; adding an electron donor to said solution; combining said stock solution and said solution; adding an agent to facilitate mixing to said solution; adding an oxygen scavenger to said solution. The color changeable dye is a first color in the presence of oxygen, capable of changing to a second color upon reduction in a substantially oxygen free environment, and capable of changing back to the first color after exposure to oxygen for a number of minutes corresponding to the intended use time of a disposable or limited use product.

Another method of producing a color changeable dye can comprise: dissolving a thickening agent in an aqueous solvent to form a solution; adding a redox indicator to said solution; adding an indicator barrier agent to said solution; adding an electron donor to said solution; adding a reduction reaction initiator to said solution; adding an agent to facilitate mixing to said solution; adding an oxygen scavenger to said solution. The color changeable dye is a first color in the presence of oxygen, capable of changing to a second color upon reduction in a substantially oxygen free environment, and capable of changing back to the first color after exposure to oxygen for a number of hours corresponding to the intended use time of a disposable or limited use product.

These and other advantages and novel features of the present invention, as well as details of illustrated embodiments thereof will be more fully understood from the following description of the drawings.

BRIEF DESCRIPTION OF SEVERAL VIEWS OF THE DRAWINGS

The patent or application file contains at least one drawing executed in color. Copies of this patent or patent application publication with color drawing(s) will be provided by the U.S. Patent and Trademark Office upon request and payment of the necessary fee.

Figure 1:
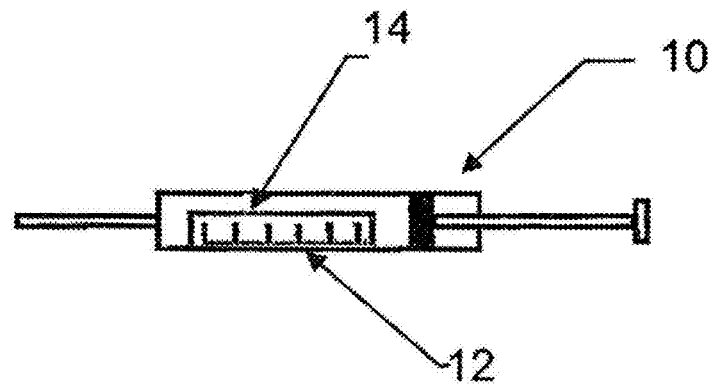
FIG. 1 is a perspective view of a syringe in accordance with one embodiment of the present invention depicting the area of the color changeable dye overlying the graduated scale of the syringe.

The foregoing summary, as well as the following detailed description of certain embodiments of the present application, will be better understood when read in conjunction with the appended drawings. For the purposes of illustration, certain embodiments are shown in the drawings. It should be understood, however, that the claims are not limited to the arrangements and instrumentality shown in the attached drawings. Furthermore, the appearance shown in the drawings is one of many ornamental appearances that can be employed to achieve the stated functions of the system.

DETAILED DESCRIPTION OF THE APPLICATION

A solution of the present application utilizes redox chemistry to create a color change indication on a product that provides accurate information or a warning to a user of, e.g.: prior use of a single use product or instrument; a reminder that a limited use product has reached its expiration time; or that a product that is restricted for use has been tampered with. The warning indication is provided by a dye that changes color in a time controlled manner wherein the dye is disposed on the product itself by being either printed on the product or incorporated within the material forming a portion of the product.

Redox reactions, or oxidation-reduction reactions, are chemical reactions where there is a change in oxidation state. For example, oxidation refers to an increase in oxidation number or the loss of electrons as represented below:

Reductant→Product+$e^-$ (Electrons lost; oxidation number increases)
Reduction refers to a decrease in oxidation number or the gain of electrons as represented below:

Oxidant+$e^-$→Product (Electrons gained; oxidation number increases)
Substances that have the ability to reduce other substances are called reducing agents, reductants or reducers. Substances that have the ability to oxidize other substances are called oxidizing agents, oxidants or oxidizers.

A color changeable dye of the present application may include a redox indicator, a reduction reaction initiator, an electron donor, oxygen scavenger, an indicator barrier agent, an agent to facilitate mixing and a thickening agent wherein the color changeable dye changes to a warning color after exposure to oxygen for a predetermined period. Each of these elements will be explored in more depth below.

A redox dye or redox indicator is a compound that changes color when it goes from its oxidized state to its reduced state and/or vice versa. For example, the oxidation and reduction of a redox indicator could be represented as follows:

Reduced Redox Indicator (colorless)→Oxidized Redox Dye (colored)+$e^-$ (Oxidation—electrons lost; oxidation number increases)

Oxidized Redox Indicator (colored)+$e^-$→Reduced Redox Dye (colorless)

(Reduction—electrons gained; oxidation number increases)

A redox indicator is incorporated into the present color changeable dye to allow for a color change upon exposure to oxygen. Examples of possible redox indicators and their corresponding colors in both the oxidized and reduced states are shown below in Table 1.

TABLE 1

| Redox Indicator | Oxidized Color | Reduced color |
|---|---|---|
| Indigo tetrasulfonate | Blue | Colorless |
| Phenosafranine | Red | Colorless |
| Methylene blue | Blue | Colorless |
| Diphenylamine | Violet | Colorless |
| 4'-Ethoxy-2,4-diaminoazobenzene | Yellow | Red |
| Diphenylamine sulfonic acid | Red-violet | Colorless |

TABLE 1-continued

| Redox Indicator | Oxidized Color | Reduced color |
|---|---|---|
| Diphenylbenzidine sulfonic acid | Violet | Colorless |
| Tris(2,2'-bipyridine)iron | Pale blue | Red |
| Tris(1,10-phenanthroline) iron (ferrion) | Pale blue | Red |
| Tris(5-nitro-1,10-phenanthroline) iron | Pale blue | Red-violet |
| Tris(2,2'-bipyridine) ruthenium | Pale blue | Yellow |

A preferred redox indicator for use in the present solution is indigo tetrasulfonate (ITS). For purposes of example, ITS will be used to explain the present solution. It is understood that other indicators could be substituted in the color changeable dye of the present application. The oxidation and reduction reactions of ITS can be simplified as follows:

Reduced ITS (colorless)→Oxidized ITS (Blue)+$e^-$ (Oxidation—electrons lost; oxidation number increases)

Oxidized ITS (Blue)+$e^-$→Reduced ITS (colorless)

(Reduction—electrons gained; oxidation number increases)

These reactions and their role in the present color changeable dye will be discussed in more detail below.

A benefit of the present application is that the redox indicator can be incorporated into the color changeable dye in its oxidized state (the blue form in the case of ITS). This is a benefit of the present application because it allows the color changeable dye to be applied to the product in the presence of oxygen. If the reduced form of a redox indicator was used in a color changeable dye, the dye would need to be applied in a substantially oxygen free environment to avoid premature oxidization of the reduced redox indicator. Applying the color changeable dye in oxygen is easier than applying the color changeable dye in an oxygen free environment. Thus, applying the oxidized form of the redox indicator is preferred. Moreover, using a redox indicator that is colored in its oxidized form, such as ITS which is blue in its oxidized form, allows the color changeable dye to be seen after application.

The product can then subsequently be packaged to provide a sterile environment for the product. The internal atmosphere of the package can be an inert gas or a vacuum such that the package provides a sealed, substantially oxygen free environment for the product. The product is then reduced to its reduced state (the colorless form in the case of ITS). In one embodiment, this can be done using ultra violet (UV) light or sunlight, as will be explained in depth below. In other embodiments, this could be done using chemical reducing agents.

When the package is subsequently opened and the product is exposed to oxygen, the dye disposed on the product will change from its reduced state (colorless for ITS) to its oxidized state (blue for ITS) after a period of time that is controlled by the composition of the dye as discussed in detail below, and that is selected to correspond to the typical time for a single use of a product in the case of single use products or that corresponds to the expiration time of the product. The time at which the dye changes color can also be selected so as to indicate that the product may have been tampered with.

Once the dye has been applied and the product has been packaged to provide a sealed, substantially oxygen free environment for the product, the color changeable dye needs to be reduced. In order to push the redox indicator to its reduced state (colorless for ITS) once it is in the sealed, substantially oxygen free environment a reduction reaction initiator and an electron donor can be included.

A reduction reaction initiator initiates the reduction of the redox indicator. An example of a reduction reaction initiator is titanium dioxide. An electron donor donates electrons to the reduction reaction initiator to allow for reduction of the redox indicator. Examples of electron donors include glycerol and sugars.

In a preferred embodiment the reduction reaction initiator is titanium dioxide and the electron donor is glycerol. When titanium dioxide and glycerol are used as the reduction reaction initiator and electron donor, the reduction reaction of the redox indicator can be initiated by exposing the dye in the sealed, substantially oxygen free environment to ultraviolet (UV) irradiation. For example, the UV irradiation creates electron-hole pairs in the titanium dioxide, $TiO_2^*(e^-, h^+)$.

$$TiO_2 + UV\ irradiation \rightarrow TiO_2^*(e^-, h^+)$$

The holes then oxidize the electron donor, glycerol, to form glyceraldehyde.

$$TiO_2^*(e^-, h^+) + C_3H_8O_3 \rightarrow TiO_2 + C_3H_6O_3$$

The photogenerated electrons then reduce the oxidized redox indicator (blue in the case of ITS) to its reduced form (colorless in the case of ITS).

$$TiO_2^-/e^- + RI_{ox} \rightarrow TiO_2 + RI_{red}$$

The dye will then stay in its reduced form (colorless in the case of ITS) until the package is opened and it is exposed to oxygen to begin the oxidation process returning it to its oxidized form (blue in the case of ITS).

A benefit of the present color change dye is that the color change can be delayed so that it does not begin immediately upon exposure to oxygen but rather at some predetermined time based on recommended use of the product. For example, the dye could turn blue after a period of days for a product that is intended to be used for a certain number of days after opening. As another example, the dye could turn blue after minutes for a product that should be used within minutes of opening. In order to delay the color change of the dye upon exposure to oxygen an oxygen scavenger and/or an indicator barrier agent can be included.

Oxygen scavengers act to delay the oxidization of the redox indicator by reacting with oxygen before allowing the oxygen to react with the redox indicator.

Examples of oxygen scavengers include sodium bisulfate, ascorbic acid, iron (II) carbonate. Preferred oxygen scavengers are sodium bisulfate, ascorbic acid and iron (II) carbonate. Sodium bisulfate readily reacts with oxygen in the following reaction:

$$2NaHSO_3 + O_2 \rightarrow 2NaHSO_4$$

Ascorbic acid readily reacts with oxygen in the following reaction:

$$C_6H_8O_6 + O_2 \rightarrow C_6H_6O_6 + H_2O_2$$

Iron (II) carbonate readily reacts with oxygen to form iron (III) carbonate. Each of these reactions proceeds more readily than reaction of ITS with oxygen. This delays the color change of the ITS.

When sodium bisulfate is used as one of the one or more oxygen scavengers it further reacts with ITS to store the ITS as its sulfonate derivative. Applicants believe this is advantageous because it assists the color change during oxidation to happen quickly. Once the color change begins, it is desirable that it progress quickly. The formation of the ITS sulfonate derivative assists in providing a quick color change.

An indicator barrier agent acts to further delay the oxidization of the redox indicator by forming a physical or chemical barrier around it. Examples of indicator barrier agents include waxes that form a physical barrier around the redox indicator and polymers that encapsulate the redox indicator. A preferred indicator barrier agent is the polymer poly(diallydimethylammonium chloride) also known as PDADMA.

PDADMA acts to create a nanoreactor in the color changeable dye. The nanoreactor created by the PDADMA aids in the reduction of the ITS and in storing the ITS and the sulfonate derivatives of ITS discussed above. The PDADMA is able to encapsulate the ITS, sodium bisulfate and sulfonate derivatives of ITS due to the electrostatic interaction between the positively charged PDADMA and the negative charges on the ITS, sulfonate derivatives of ITS and the sodium bisulfate. The encapsulation by PDADMA forms the nanoreactor. This allows for efficient reduction of the ITS and creates a protective capsule around the ITS.

Other agents can be added to the color changeable dye in order to give the dye physical properties that make it usable for its intended purpose. For example, a thickening agent can be added to the dye to give it a workable consistency. A preferred thickening agent is 2-hydroxyethyl cellulose.

As another example of an agent that gives the dye physical properties that make it usable for its intended purpose, an agent to facilitate mixing lessens the tacky nature of the redox indicator and creates microspheres to help the hygroscopic glycerol mix with an aqueous solvent and form a usable solution. Examples of agents to facilitate mixing include bentonite nanoclay, glass microspheres and cellulose acetate. A preferred agent to facilitate mixing is bentonite nanoclay. The bentonite nanoclay acts to incorporate the viscous, hygroscopic glycerol into the aqueous dye. Without addition of an agent to facilitate mixing, such as bentonite nanoclay, the other components of the solution will not mix well. The redox indicator, reduction reaction initiator, electron donor and thickening agent will not mix with the oxygen scavenger. They separate like a mixture of oil and water. The agent for facilitating mixing, such as bentonite nanoclay, allows these materials to be mixed and form the present color changeable dye. As a specific example, titanium dioxide, glycerol, ITS and hydroxyethyl cellulose will not physically mix with the ascorbic acid and sodium bisulfate. The mixing can be accomplished by adding bentonite nanoclay and exposing the solution to sonication.

For single use disposable products the dye may be required to be substantially translucent after reduction in its substantially oxygen free environment and change color after exposure to oxygen after a number of minutes, a number of hours, or a week.

Figure 2:
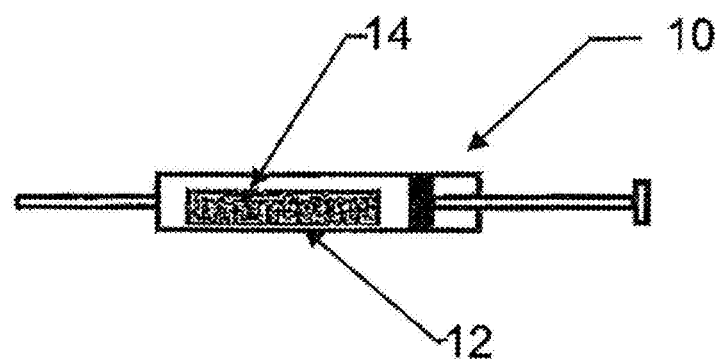
FIG. 2 is a perspective view of the syringe of FIG. 1 depicting the syringe after the timed color change occurs.

For example, the color changeable dye that changes after exposure to oxygen for a number of minutes could be used with a disposable syringe that is intended for a single use that takes less than 10 minutes. FIG. 1 shows such a disposable syringe 10. The disposable syringe 10 can include a graduated scale 12 printed thereon so that the amount of liquid drawn into the syringe can be accurately measured. In one embodiment, the color changeable dye 14 is printed over the scale. In this embodiment, the dye is substantially translucent so that the scale is clearly visible until the dye 14 changes color, as depicted at 14' in FIG. 2, after a predetermined time associated with the time of typical use of the single use disposable syringe 10. In the embodiment of the syringe depicted in FIGS. 1 and 2, because the dye is disposed over the graduated scale, when the time controlled color change occurs, the graduated scale is no longer clearly visible so that the disposable syringe cannot be accidentally reused. In this manner, the transmission of contaminants or disease from one patient to another by an inadvertent reuse of the syringe is prevented.

Figure 3:
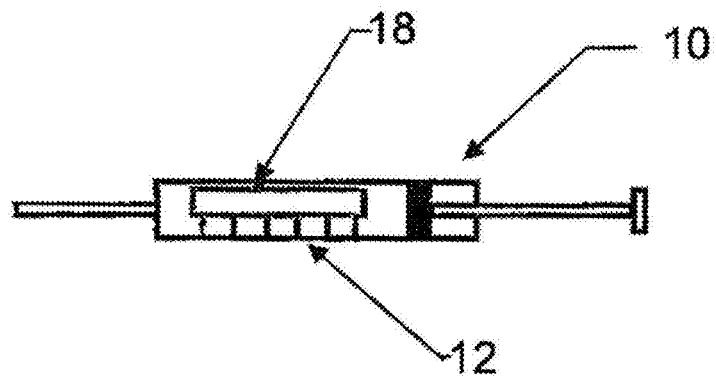
FIG. 3 is an illustration of an alternative placement of the dye on a syringe.
Figure 4:
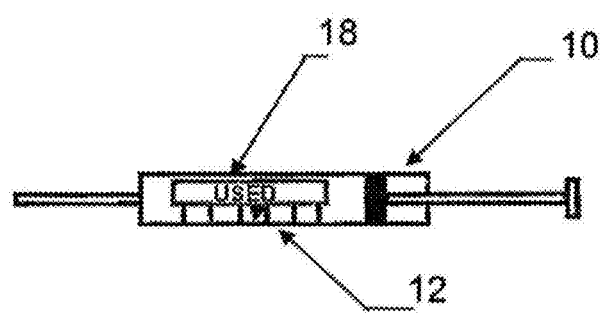
FIG. 4 is an illustration of the syringe of FIG. 3 with an expiration message printed with the color changeable dye which becomes visible after a predetermined period of time.

In another embodiment of the present invention as depicted in FIGS. 3 and 4, the dye is disposed on another area such as 18 of the disposable syringe 10. The dye can be used as an ink to print a message on the disposable product so that when the color change occurs the message, such as the word "USED," becomes visible to the user as shown at 18' in FIG. 4.

Figure 5:
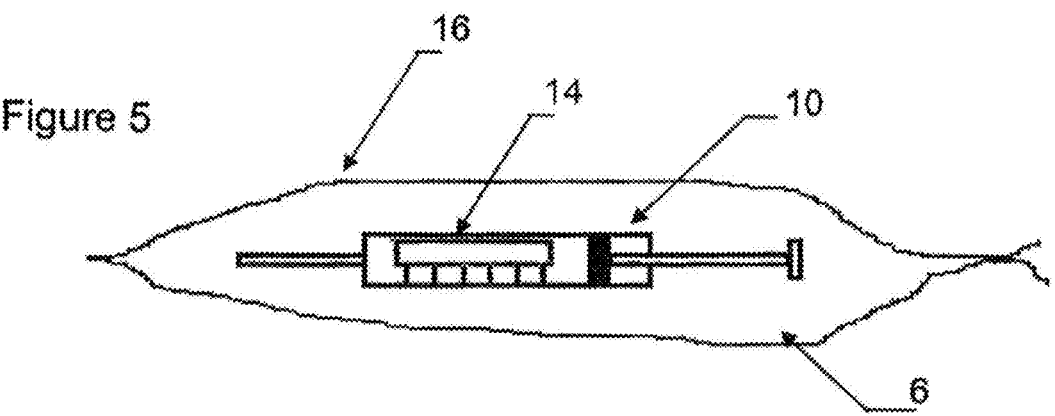
FIG. 5 is a perspective view of the syringe of FIG. 3 contained in a package to prevent premature actuation of the color changeable dye.

The dye of the present invention is applied in its colored oxidized form (blue for ITS) and dries quickly after being placed on the product. After it is dry, the product can be sterilized with any common, low temperature sterilization technique and then placed in a sealed container or package 16, as depicted in FIG. 5, with an internal atmosphere of an inert gas or a vacuum. In the sealed, substantially oxygen free package, the dye is reduced. This can be done by exposure to UV light or sunlight as discussed above. The color changeable dye will then turn translucent or "water white". When the package is subsequently opened and the product is exposed to oxygen, the dye disposed on the product will change from substantially translucent or "water white" to its colored form (blue for ITS) after five or ten minutes depending upon the makeup of the solution.

Figure 6:
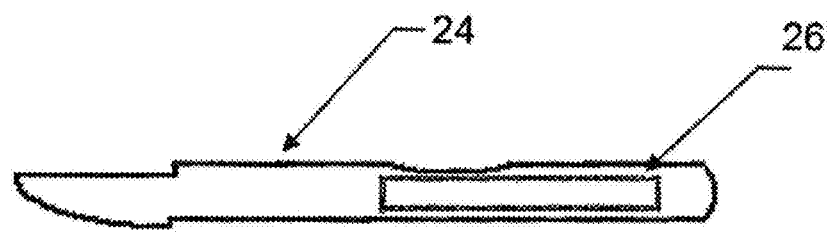
FIG. 6 is a perspective view of a scalpel with the color changeable dye in accordance with another embodiment of the present invention.
Figure 7:
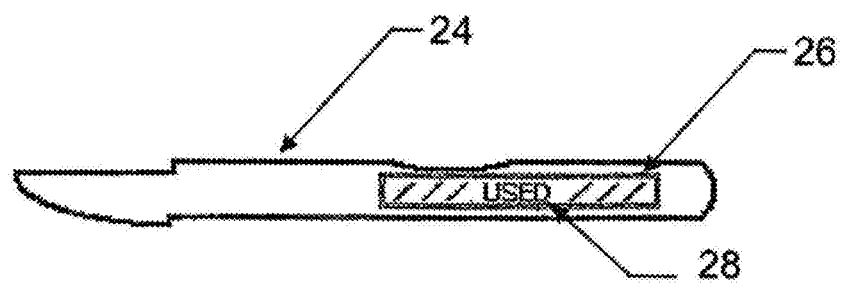
FIG. 7 is a perspective view of the scalpel of FIG. 6 with a message printed with the color changeable dye which has become visible after a predetermined time.

As another example, the color changeable dye that changes after exposure to oxygen for a number of hours could be used with a disposable scalpel that is intended for use in a surgery that takes hours to complete. Such a disposable scalpel is depicted in FIG. 6. The disposable scalpel 24 has the dye 26 of the present invention disposed thereon in an area that will be clearly visible to the surgeon when the dye changes color. As depicted in FIG. 7, a warning message 28 may be printed with the dye on the scalpel to inform the surgeon that the scalpel has been "USED" wherein the color change occurs after a certain number of hours after the scalpel is removed from a substantially oxygen free package or container as discussed above with respect to the syringe. In this way, the surgeon is warned that the scalpel should not be inadvertently used again but should be disposed of.

Figure 8:
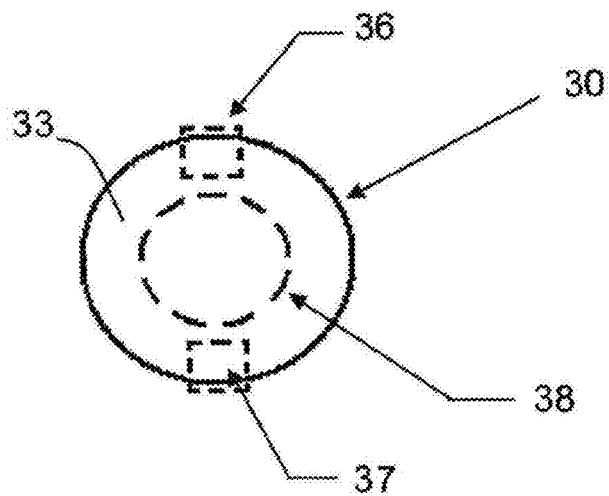
FIG. 8 is a front perspective view of a contact lens in accordance with one embodiment of the present invention with the dye in peripheral areas of the contact lens.
Figure 9:
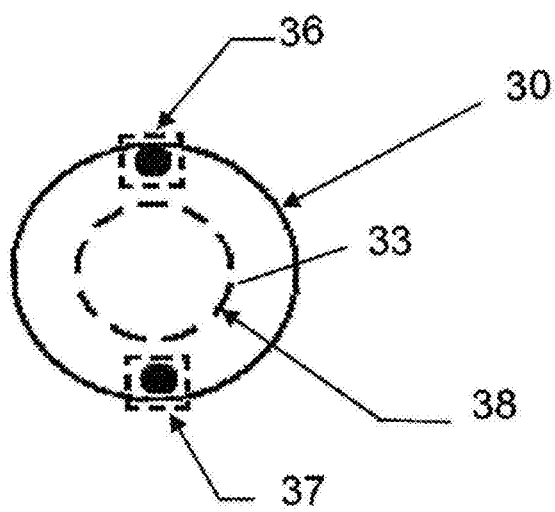
FIG. 9 is a front perspective view of the contact lens of FIG. 8 depicting the dye after color change has occurred to indicate expiration of the lens.
Figure 10:
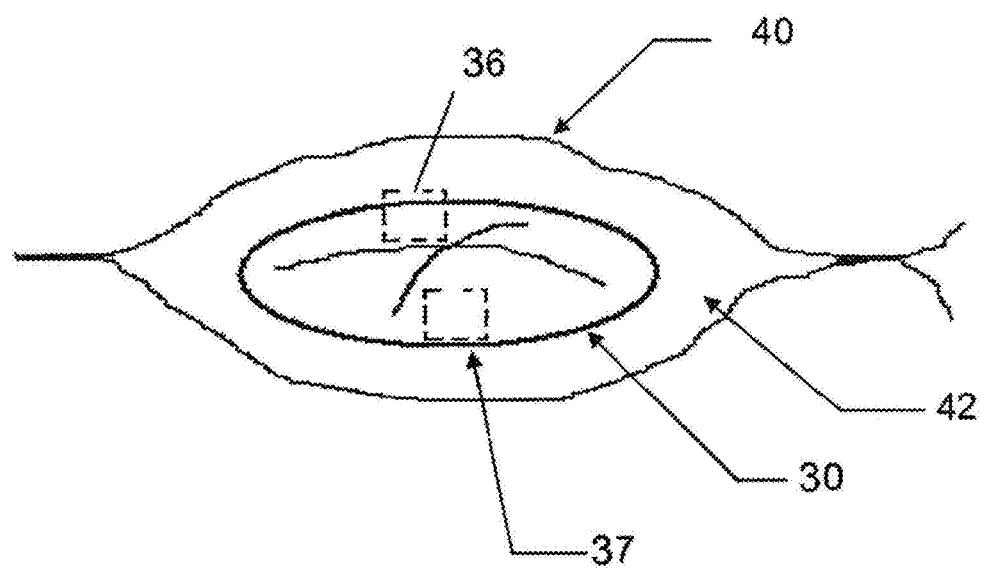
FIG. 10 is a cross-sectional view of a package containing the contact lens of FIG. 8 to prevent premature color change.
Figure 11:
FIG. 11 is a photograph of a color changeable dye of one embodiment of the present invention after approximately 26 seconds of exposure to oxygen.
Figure 12:
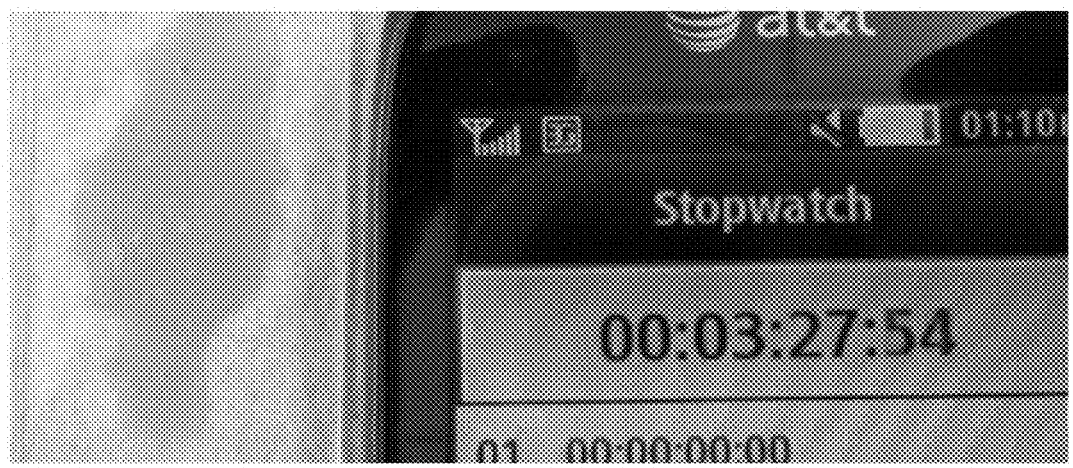
FIG. 12 is a photograph of a color changeable dye of one embodiment of the present invention after approximately 3 minutes and 28 seconds of exposure to oxygen.
Figure 13:
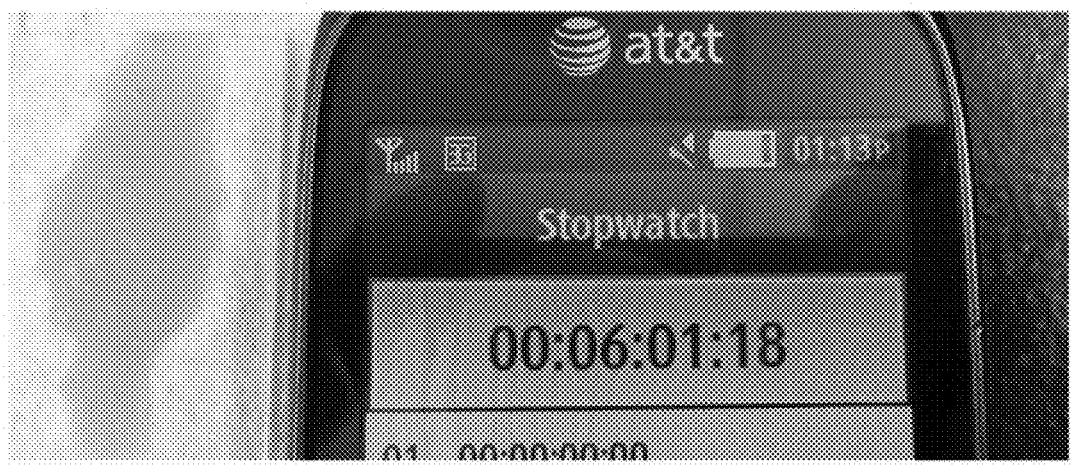
FIG. 13 is a photograph of a color changeable dye of one embodiment of the present invention after approximately 6 minutes 1 second of exposure to oxygen.
Figure 14:
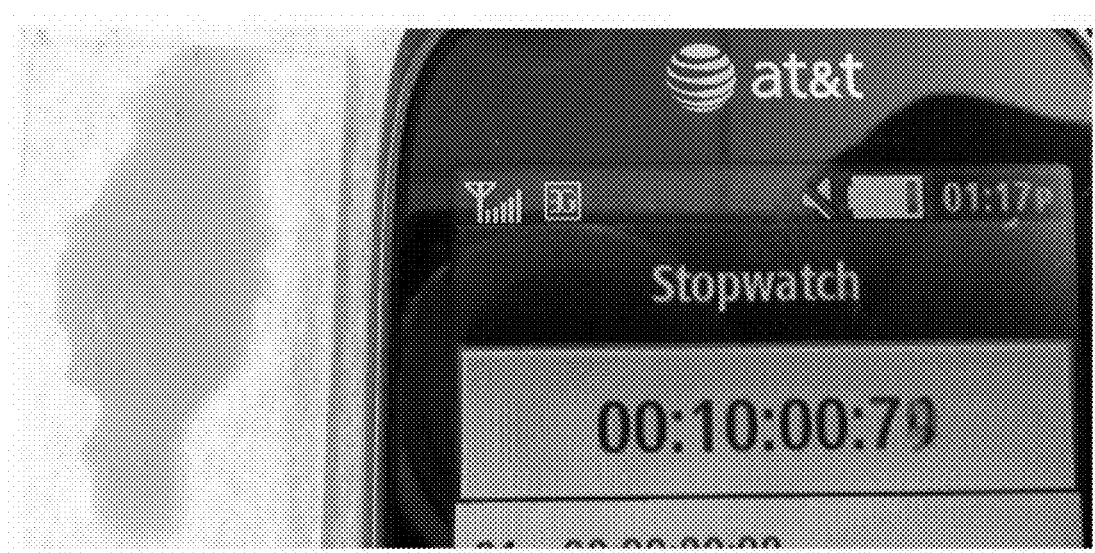
FIG. 14 is a photograph of a color changeable dye of one embodiment of the present invention after approximately 10 minutes and 1 second of exposure to oxygen.
Figure 15:
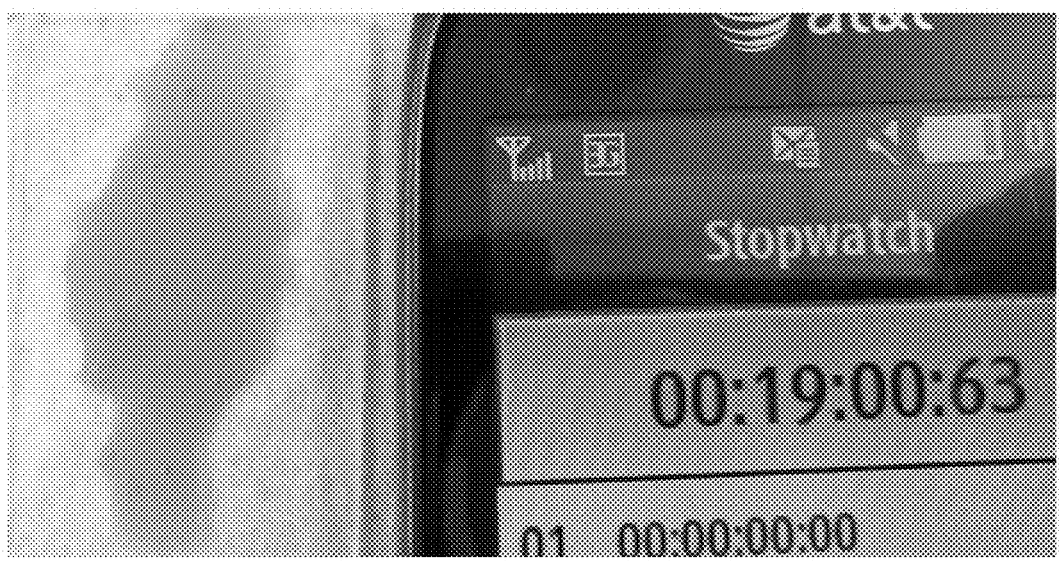
FIG. 15 is a photograph of a color changeable dye of one embodiment of the present invention after approximately 19 minutes and 1 second of exposure to oxygen.
Figure 16:
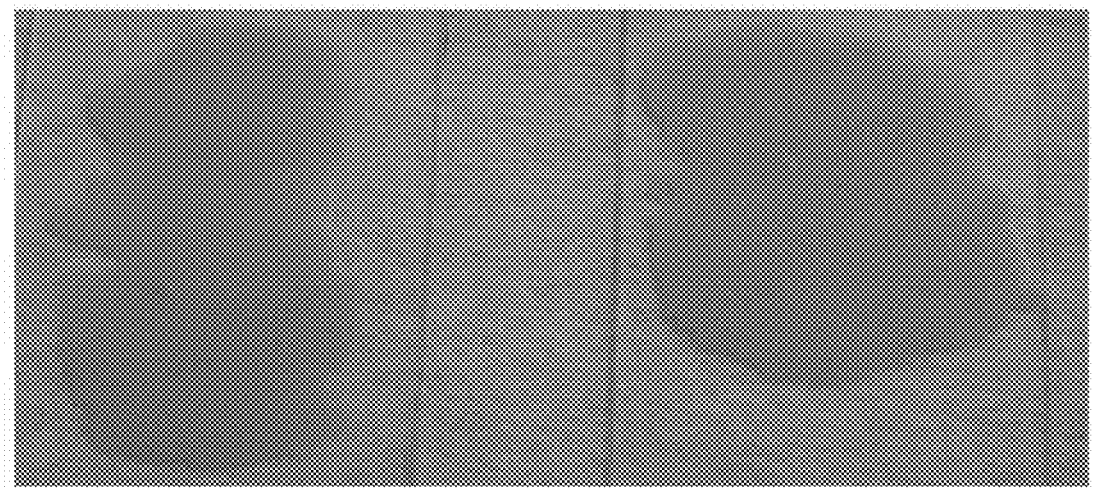
FIG. 16 is a photograph of a color changeable dye of one embodiment of the present invention after approximately 10 minutes of exposure to oxygen.
Figure 17:
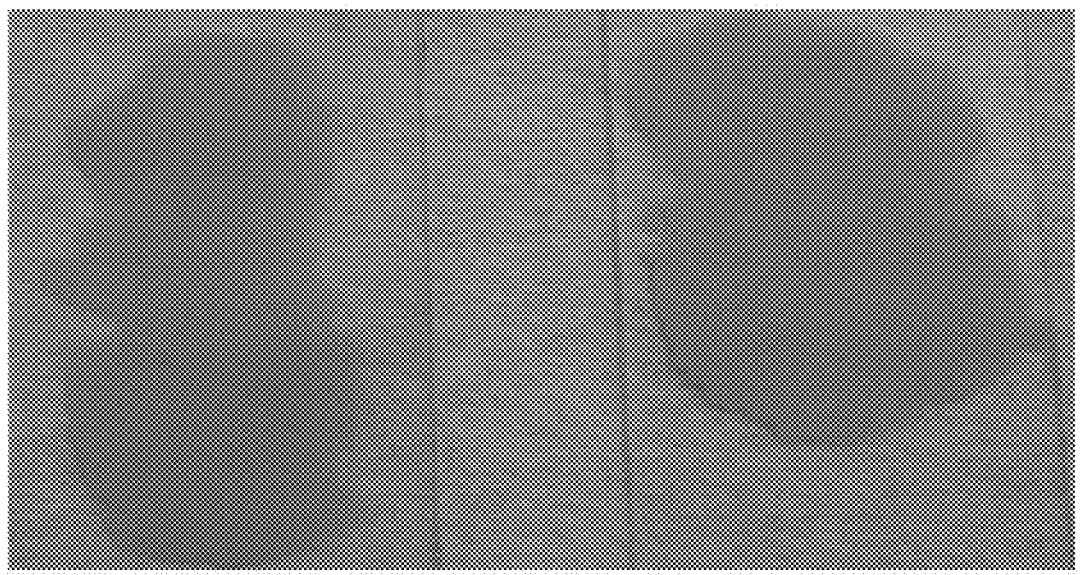
FIG. 17 is a photograph of a color changeable dye of one embodiment of the present invention after approximately 1 hour 29 minutes of exposure to oxygen.
Figure 18:
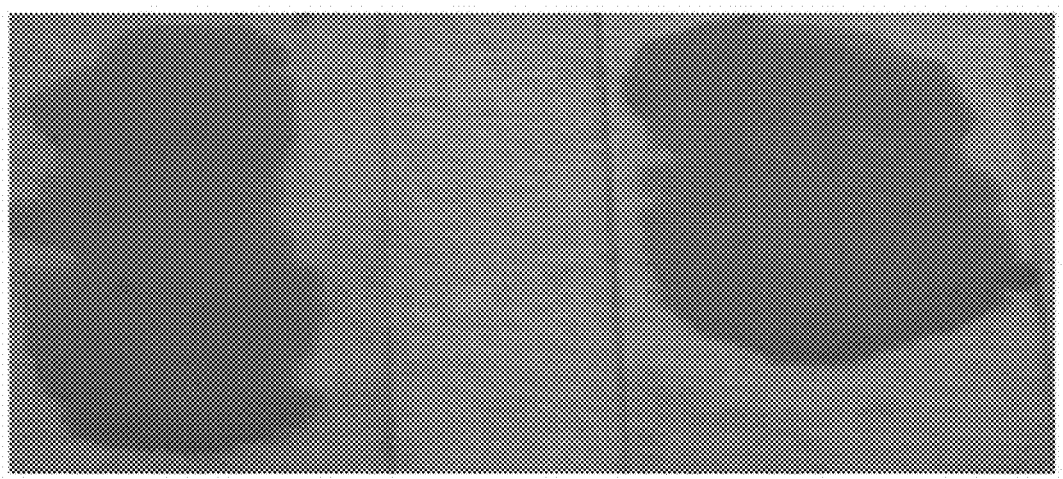
FIG. 18 is a photograph of a color changeable dye of one embodiment of the present invention after approximately 2 hours 20 minutes of exposure to oxygen.
Figure 19:
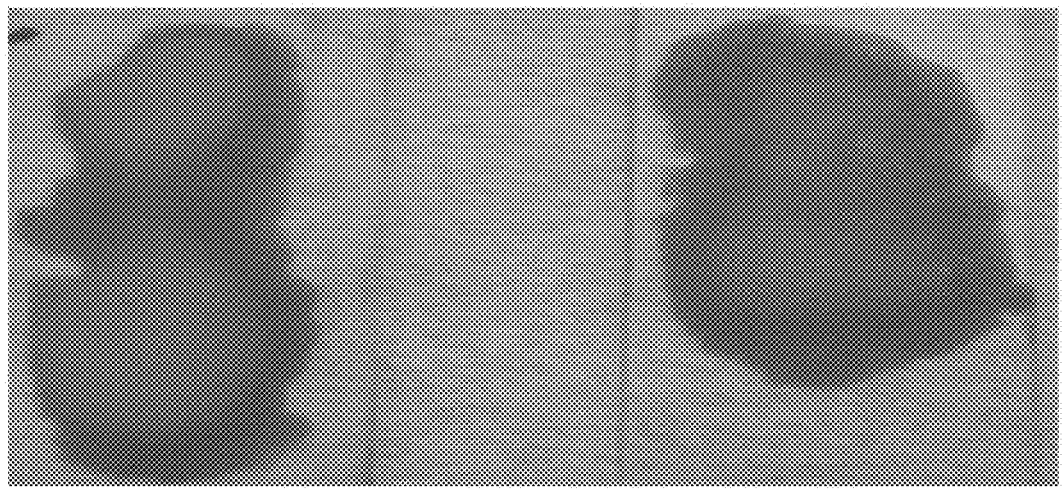
FIG. 19 is a photograph of a color changeable dye of one embodiment of the present invention after approximately 4 hours 10 minutes of exposure to oxygen.
Figure 20:
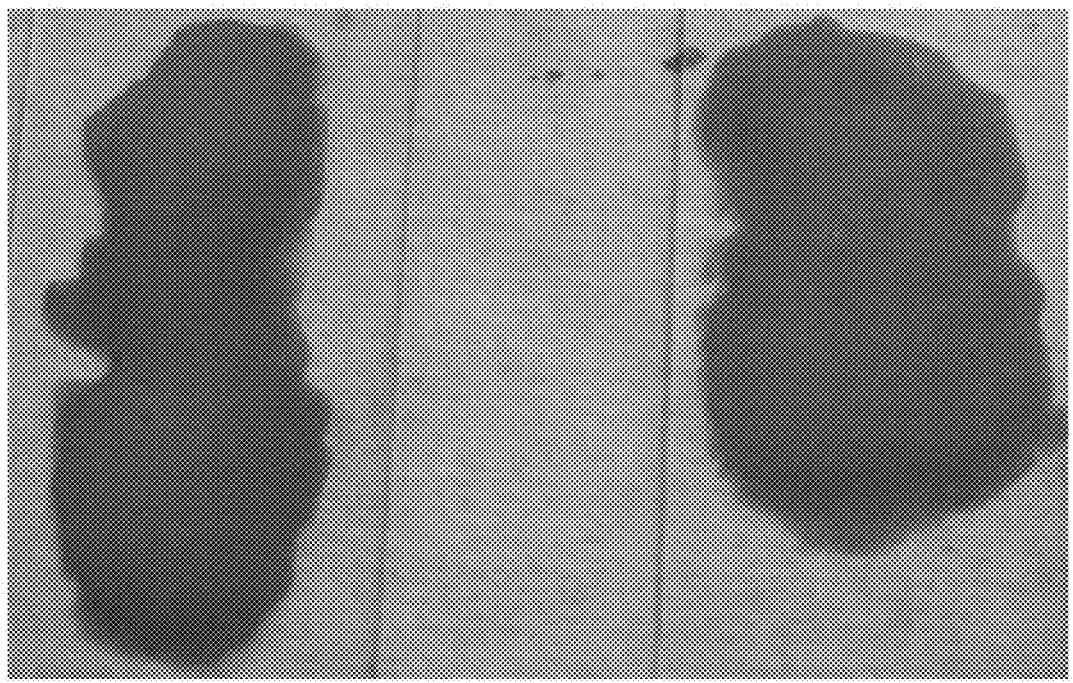
FIG. 20 is a photograph of a color changeable dye of one embodiment of the present invention after approximately 11 hours 40 minutes of exposure to oxygen.
Figure 21:
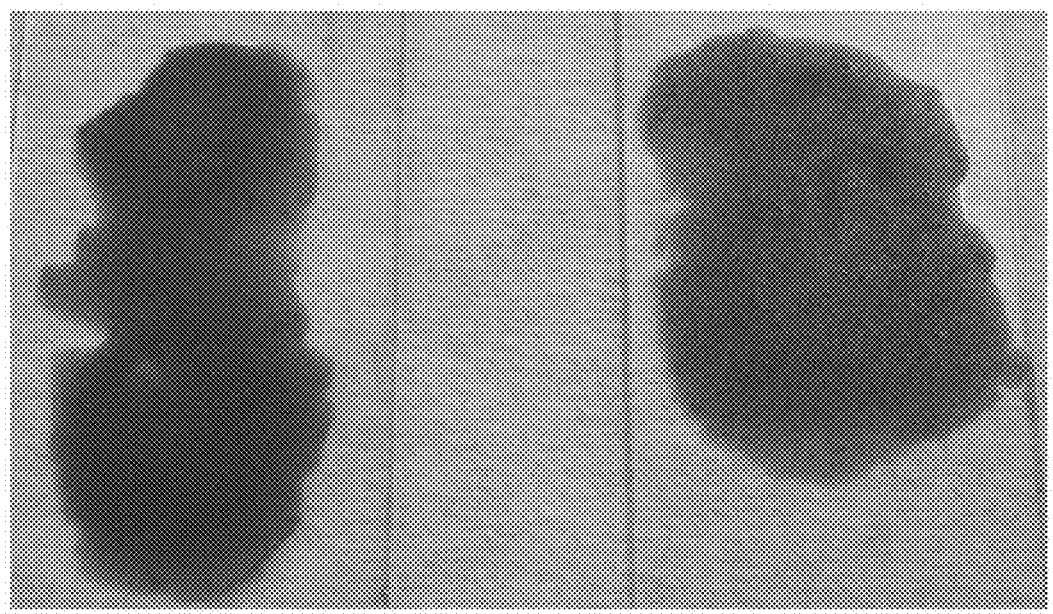
FIG. 21 is a photograph of a color changeable dye of one embodiment of the present invention after approximately 23 hours of exposure to oxygen.

As yet another example, the color changeable dye that changes after exposure to oxygen for a number of days or a week could be used with a disposable contact lens that is only intended for use for a certain number of days or weeks. Such lenses are known as "daily wear" or "monthly wear" disposable contact lenses. The problem that arises with these disposable contact lenses is that many users of the contact lens do not dispose of the contact lens at the recommended time but wear the contact lens longer than they are supposed to. This can damage the eye. The contact lens of the present invention as depicted in FIGS. 8-10 overcomes this problem by providing a visual indication on the contact lens itself that the contact lens should be removed from the eye after the contact lens has been worn for the prescribed amount of time.

In accordance with the present invention, the color changeable dye 36 as described above is disposed on a portion of the contact lens. The formulation for the dye is preferably that which delays the color change of the dye for a certain number of days or weeks according to the longest time that the contact lens manufacturer suggests that the contact lenses should be worn. When the dye is originally applied it will be applied in its colored state (blue for ITS) allowing the manufacturer to see the applied dye. As discussed above for the other devices, the contact lens 30 should be placed in a substantially oxygen free package 40 as shown in FIG. 10. In the sealed, substantially oxygen free package, the dye is reduced. This can be done by exposure to UV light or sunlight as discussed above. The color changeable dye will then turn translucent or "water white". The user of the contact lens 30 can then remove the contact lens from the package for immediate use in the eye. After the contact lens has been worn in the eye for the recommended time by the manufacturer, the color change of the dye occurs as depicted in FIG. 9 wherein, colored (blue for ITS) spots are clearly visible on the contact lens by an observer looking into the contact lens wearer's eye. As such, the contact lens wearer is encouraged to remove the contact lens from his eye and dispose of it as recommended.

As yet another example, the color changeable dye that changes after exposure to oxygen for a number of hours or a week could be used with a product such as makeup or medicine that has a shelf life of certain period of time. For example, it has been found that cosmetic applicators can harbor bacteria that can infect the eye. The dye of the present invention can be applied to the handle of a mascara applicator or eyeliner applicator, for example, so that a warning message becomes visible at the recommended time of replacement, after a number of hours or a week. As such a user is warned that the cosmetic should be disposed of prior to its expiration to prevent eye infections. With regard to medications, the present dye could be applied to oral medications such as pills wherein the dye is printed directly onto the pill and changes color from white or translucent to another darker color or warning symbol when the environmental oxygen level around the pill changes. The color change indication of the dye should be timed to coincide with the expiration of the pills.

It is understood that one can vary particular aspects or volumes of the components of the color changeable dye in order to vary the timing of the color change after exposure to oxygen between a number of minutes, a number of hours or a week. For example, one could vary the type, number or amount of oxygen scavenger(s) used in the color changeable dye to vary the timing of the color change. As another example, one could also vary the type, number or amount of indicator barrier agent(s) used in the color changeable dye. As another example, where a polymeric indicator barrier agent is used variations in the molecular weight of the polymer could also be used to vary the timing of the color change.

For example, a single use disposable products where the dye is required to be substantially translucent after reduction in its sealed substantially oxygen free packaging and wherein the dye is to change color after exposure to oxygen after a number of minutes, the dye solution can be formed as follows.

First, a stock solution can be prepared by dissolving a redox indicator and thickening agent in an aqueous solvent. The stock solution can then be stirred vigorously for a period of time followed by gentle stirring for a second period of time. The stock solution can then be mixed to eradicate any layer separation. These steps can be performed in this order or another order.

The redox indicators discussed above could be used in preparing the present stock solution. In one embodiment the redox indicator is ITS. An amount of redox indicator effective to create a color changeable dye that changes to a warning color after exposure to oxygen for a number of minutes corresponding to the intended use time of a disposable or limited use product is added. For example, 0.4-0.6 gram of redox indicator can be added, preferably 0.475-0.525 gram, or more preferably 0.5 gram. In one embodiment, the redox indicator has a purity of approximately 85%.

The thickening agents discussed above could be used in preparing the present stock solution. In one embodiment the thickening agent is 2-hydroxymethylcellulose. An amount of thickening agent effective to create a color changeable dye that changes to a warning color after exposure to oxygen for a number of minutes corresponding to the intended use time of a disposable or limited use product is added. For example, 4-6 grams of thickening agent can be added, preferably 4.7-5.3 grams, or more preferably 5 grams. In one embodiment, the thickening agent has a molecular weight of approximately 90,000 grams per mole.

The aqueous solvent can be distilled and or deionized water. In one embodiment the distilled deionized water is generated from a double reverse osmosis system. An amount of aqueous solvent effective to create a color changeable dye that changes to a warning color after exposure to oxygen for a number of minutes corresponding to the intended use time of a disposable or limited use product is added. For example, 47-143 milliliters of an aqueous solvent can be added, preferably 76-114 milliliters, or more preferably 95 milliliters.

The vigorous stirring can occur for 25-35 minutes or preferably 30 minutes. The gentle stirring can occur for 6-10 hours or preferably overnight.

To prepare the color changeable dye, a reduction reaction initiator can first be mixed with an indicator barrier agent. An electron donor can then be added. The stock solution can then be added. The solution can then be stirred vigorously. An agent to facilitate mixing can then be added to the solution. The solution can then be sonicated. An oxygen scavenger can then be added to the solution. The solution can then be mixed. The solution can then be applied thinly to a limited use or disposable product and allowed to dry. These steps can be performed in this order or another order.

The reduction reaction initiators discussed above could be used in preparing the present color changeable dye. In one embodiment the reduction reaction initiator is titanium dioxide. The titanium dioxide can be ground using a mortar and pestle. The titanium dioxide can be ground to greater than 100 nanometer particles. In one embodiment, the titanium dioxide is an anatase/rutile mixture. In one embodiment the titanium dioxide is 99.5% pure. An amount of reduction reaction initiator effective to create a color changeable dye that changes to a warning color after exposure to oxygen for a number of minutes corresponding to the intended use time of a disposable or limited use product is added. For example, 0.16-0.24 gram of reduction reaction initiator can be added, preferably 0.19-0.21 gram, or more preferably 0.2 gram. When the titanium dioxide is present from 0.16-0.24 gram the other components of the solution should be closer to the preferred concentrations.

The indicator barrier agents discussed above could be used in preparing the present color changeable dye. In one embodiment, the indicator barrier agent is PDADMA. The PDADMA can be high molecular weight (400,000-500,000 grams per mole). The PDADMA can be supplied as a 20% solution in deionized water. An amount of indicator barrier agent effective to create a color changeable dye that changes to a warning color after exposure to oxygen for a number of minutes corresponding to the intended use time of a disposable or limited use product is added. For example, 0.8-1.2 gram of indicator barrier agent can be added, preferably 0.9-1.1 gram, or more preferably 1 gram.

The electron donors discussed above could be used in preparing the present color changeable dye. In one embodiment, the electron donor is glycerol. An amount of electron donor effective to create a color changeable dye that changes to a warning color after exposure to oxygen for a number of minutes corresponding to the intended use time of a disposable or limited use product is added. For example, 1.6-2.4 grams of electron donor can be added, preferably 1.9-2.1 grams, or more preferably 2 grams.

An amount of stock solution effective to create a color changeable dye that changes to a warning color after exposure to oxygen for a number of minutes corresponding to the intended use time of a disposable or limited use product is added. For example, 16-24 grams of stock solution can be added, preferably 19-21 grams, or more preferably 20 grams.

The vigorous stirring can occur for 10-20 minutes or preferably 15 minutes.

The agents to facilitate mixing discussed above could be used in preparing the present color changeable dye. In one embodiment, the agent to facilitate mixing is bentonite (nanoclay powder). The bentonite can be ground using a mortar and pestle. An amount of agent to facilitate mixing to create a color changeable dye that changes to a warning color after exposure to oxygen for a number of minutes corresponding to the intended use time of a disposable or limited use product is added. For example, 0.8-1.2 gram of an agent to facilitate mixing can be added, preferably 0.9-1.1 gram, or more preferably 1 gram. Sonication can aid in mixing of the bentonite. The solution can be sonicated for 25-45 minutes or preferably 35 minutes.

The oxygen scavengers discussed above could be used in preparing the present color changeable dye. In one embodiment, the oxygen scavengers are sodium bisulfate and L-ascorbic acid. An amount of oxygen scavenger effective to create a color changeable dye that changes to a warning color after exposure to oxygen for a number of minutes corresponding to the intended use time of a disposable or limited use product is added. For example, 0.08-0.12 gram of sodium bisulfate can be added, preferably 0.09-0.10 gram, or more preferably 0.1 gram. As another example, 0.72-1.08 gram of L-ascorbic acid can be added, preferably 0.85-0.95 gram, or more preferably 0.9 gram.

The solution can be mixed under argon or in the presence of oxygen. This mixing can last for 25-35 minutes or preferably 30 minutes. The solution can be spread thin and allowed to dry under argon or in the presence of oxygen. The drying can last for hours, preferably 1-2 hours.

FIGS. 11-15 are photographs of one embodiment of the color changeable dye described above at approximately 26 seconds, 3 minutes and 28 seconds, 6 minutes 1 second, 10 minutes and 1 second and 19 minutes and 1 second of exposure to oxygen respectively. The ink can be translucent, water white or light yellow when dried. After exposure to oxygen the color change can be visible after 3-4 minutes. Color change to green blue can be complete after 10-15 minutes. The specific time required can also be dependent on the thickness of the film.

If the solution is not mixed under argon the redox indicator will oxidize to the oxidized colored state (blue for ITS). This can then be reversed by putting the dye in the substantially oxygen free argon environment, such as the product packaging, and exposing it to UV light or sunlight. The dye will then change back to the translucent, water white or light yellow color. When removed from the substantially oxygen free argon environment, the dye can then change back to the colored (blue) oxidized state as discussed above.

As another example, in order to delay the time at which the dye changes color upon exposure to oxygen to a number of hours the solution can be formed as follows.

First a stock solution can be prepared by dissolving thickening agent in an aqueous solvent. The stock solution can then be stirred vigorously for a period of time followed by gentle stirring for a second period of time. The stock solution can then be mixed to eradicate any layer separation. These steps can be performed in this order or another order.

The thickening agents discussed above could be used in preparing the present stock solution. In one embodiment the thickening agent is 2-hydroxymethylcellulose. An amount of thickening agent effective to create a color changeable dye that changes to a warning color after exposure to oxygen for a number of hours corresponding to the intended use time of a disposable or limited use product is added. For example, 4-6 grams of thickening agent can be added, preferably 4.7-5.3 grams, or more preferably 5 grams. In one embodiment, the thickening agent has a molecular weight of approximately 90,000 grams per mole.

The aqueous solvent can be distilled and or deionized water. In one embodiment the distilled deionized water is generated from a double reverse osmosis system. An amount of aqueous solvent effective to create a color changeable dye that changes to a warning color after exposure to oxygen for a number of hours corresponding to the intended use time of a disposable or limited use product is added. For example, 47-143 milliliters of an aqueous solvent can be added, preferably 76-114 milliliters, or more preferably 95 milliliters.

The vigorous stirring can occur for 25-35 minutes or preferably 30 minutes. The gentle stirring can occur for 6-10 hours or preferably overnight.

To prepare the color changeable dye, a redox indicator can first be mixed with the stock solution. An indicator barrier agent can then be added. An electron donor can then be added. The solution can then be stirred. A reduction reaction initiator can then be added. An agent to facilitate mixing can then be added. The solution can then be stirred. The solution can then be sonicated. An oxygen scavenger can then be added to the solution. The solution can then be mixed. The solution can then be applied thinly to a limited use or disposable product and allowed to dry. These steps can be performed in this order or another order.

The redox indicators discussed above could be used in preparing the present color changeable dye. In one embodiment the redox indicator is ITS. An amount of redox indicator effective to create a color changeable dye that changes to a warning color after exposure to oxygen for a number of hours corresponding to the intended use time of a disposable or limited use product is added. For example, 0.06-0.09 gram of redox indicator can be added, preferably 0.071-a 0.079 gram, or more preferably 0.075 grams. In one embodiment, the redox indicator has a purity of approximately 85%.

An amount of stock solution effective to create a color changeable dye that changes to a warning color after exposure to oxygen for a number of hours corresponding to the intended use time of a disposable or limited use product is added. For example, 17-25.6 grams of stock solution can be added, preferably 20.2-22.4 grams, or more preferably 21.3 grams. In another embodiment, 8-12 grams of stock solution is mixed with 9.2-13.8 grams of an aqueous solvent before adding the redox indicator, preferably 9.5-10.5 grams of stock solution is mixed with 10.9-12.1 grams of an aqueous solvent before adding the redox indicator, or more preferably, 10.0 grams of stock solution is mixed with 11.5 grams of an aqueous solvent before adding the redox indicator The indicator barrier agents discussed above could be used in preparing the present color changeable dye. In one embodiment, the indicator barrier agent is PDADMA. The PDADMA can be high molecular weight (400,000-500,000 grams per mole). The PDADMA can be supplied as a 20% solution in deionized water. An amount of indicator barrier agent effective to create a color changeable dye that changes to a warning color after exposure to oxygen for a number of hours corresponding to the intended use time of a disposable or limited use product is added. For example, 2-3 grams of indicator barrier agent can be added, preferably 2.4-2.6 grams, or more preferably 2.5 grams.

The electron donors discussed above could be used in preparing the present color changeable dye. In one embodiment, the electron donor is glycerol. An amount of electron donor effective to create a color changeable dye that changes to a warning color after exposure to oxygen for a number of hours corresponding to the intended use time of a disposable or limited use product is added. For example, 2.1-4.3 grams of electron donor can be added, or preferably 2.5-3.8 grams, or more preferably approximately 2.6 grams, approximately 3.1 grams, or approximately 3.6 grams.

The stirring can occur for 4-6 minutes or preferably 5 minutes.

The reduction reaction initiators discussed above could be used in preparing the present color changeable dye. In one embodiment the reduction reaction initiator is titanium dioxide. The titanium dioxide can be ground using a mortar and pestle. The titanium dioxide can be ground to greater than 100 nanometer particles. In one embodiment, the titanium dioxide is an anatase/rutile mixture. In one embodiment the titanium dioxide is 99.5% pure. An amount of reduction reaction initiator effective to create a color changeable dye that changes to a warning color after exposure to oxygen for a number of hours corresponding to the intended use time of a disposable or limited use product is added. For example, 0.21-0.31 gram of reduction reaction initiator can be added, preferably 0.25-0.27 gram, or more preferably approximately 0.26 gram. When the titanium dioxide is present from 0.21-0.31 gram the other components of the solution should be closer to the preferred concentrations.

The agents to facilitate mixing discussed above could be used in preparing the present color changeable dye. In one embodiment, the agent to facilitate mixing is bentonite (nanoclay powder). The bentonite can be ground using a mortar and pestle. An amount of agent to facilitate mixing to create a color changeable dye that changes to a warning color after exposure to oxygen for a number of hours corresponding to the intended use time of a disposable or limited use product is added. For example, 1-8-2.8 grams of an agent to facilitate mixing can be added, preferably 2.2-2.4 grams, or more preferably 2.3 grams. Stirring and sonication can aid in mixing of the bentonite. The solution can be stirred for a number of minutes, preferably 1 minute. The solution can be sonicated for 25-35 minutes or preferably 30 minutes.

The oxygen scavengers discussed above could be used in preparing the present color changeable dye. In one embodiment, the oxygen scavengers are sodium bisulfate and L-ascorbic acid. An amount of oxygen scavenger effective to create a color changeable dye that changes to a warning color after exposure to oxygen for a number of minutes corresponding to the intended use time of a disposable or limited use product is added. For example, 0.35-0.53 gram of L-ascorbic acid can be added, preferably 0.42-0.46 gram, or more preferably approximately 0.44 gram. Mixing can occur before or after addition of an additional oxygen scavenger. The mixing could occur in air and last for 30-60 seconds. The solution should be in the colored oxidized state at this point (blue/green if ITS is being used). 0.28-0.48 grams of sodium bisulfate can then be added, preferably 0.33-0.38 grams, or more preferably approximately 0.35 gram or approximately 0.4 gram.

The solution can be mixed under argon or in oxygen. This mixing can last for 25-35 minutes or preferably 30 minutes. The solution can be spread thin and allowed to dry under argon or in oxygen. The drying can last for 6-10 hours or preferably overnight. The color changeable dye will be in its oxidized colored state (blue for ITS). This can be reversed by exposing the dye to UV light or sunlight while in the substantially oxygen free argon environment, such as the packaging for the disposable or limited use product. This will cause the dye to change back to the translucent, water white, light yellow or yellow orange color.

FIGS. 16-21 are photographs of one embodiment of the color changeable dye described above at approximately 10 minutes, 1 hour 29 minutes, 2 hours 20 minutes, 4 hours 10 minutes, 11 hours 40 minutes and 23 hours of exposure to oxygen respectively. The ink can be translucent, water white, light yellow or orange/yellow when dried. After exposure to oxygen, the color change can begin to occur in the 2-3 hour range. The specific time required can also be dependent on the thickness of the film.

The present color changeable dye can be applied to a disposable, limited or restricted use product. The present color changeable dye can be applied to the product using a number of methods known in the present art. For example, the solution can be applied to the product by printing, painting, spraying, deposition, dipping, flowing or another method known in the art.

Example 1

In one example, a dye that was substantially translucent in a substantially oxygen free environment and changed color after exposure to oxygen after a number of minutes was formed as follows.

First a stock solution was prepared by dissolving 0.5 grams of ITS and 5 grams of 2-hydroxylmethylcellulose in 95 milliliters of distilled water. The ITS had a purity of 85%. The 2-hydroxymethylcellulose had a molecular weight of approximately 90,000 grams per mole. The distilled deionized water was generated from a double reverse osmosis system. The stock solution was stirred vigorously for 30 minutes and then stirred gently overnight. The stock solution was then mixed to eradicate any layer separation.

To prepare the color changeable dye, 0.2 gram titanium dioxide was ground using a mortar and pestle. The titanium dioxide was ground to greater than 100 nanometer particles. The titanium dioxide was an anatase/rutile mixture and was 99.5% pure. 1 gram of high molecular weight (400,000-500,000 grams per mole) PDADMA supplied as a 20% solution in deionized water was added to the titanium dioxide. 2 grams of glycerol were also added. 20 grams of the stock solution were then added. The solution was stirred vigorously for 15 minutes. 1 gram of crushed bentonite (crushed using a mortar and pestle) was then added. The solution was sonicated for 35 minutes. 0.1 gram of sodium bisulfate was then added along with 0.9 gram of L-ascorbic acid. The solution was mixed under argon for 30 minutes. The solution was spread thin and allowed to dry under argon for 1-2 hours.

FIGS. 11-15 are photographs of the color changeable dye described above at approximately 26 seconds, 3 minutes and 28 seconds, 6 minutes 1 second, 10 minutes and 1 second and 19 minutes and 1 second of exposure to oxygen respectively. The ink was translucent, water white or light yellow when dried. After exposure to oxygen the color change was visible after 3-4 minutes. Color change to green blue was complete after 10-15 minutes. The specific time required can also be dependent on the thickness of the film.

If the solution had not been mixed under argon the ITS would have oxidized to the oxidized colored state (blue). This could have been reversed by putting the dye in the substantially oxygen free argon environment and exposing it to UV light or sunlight. The dye would have then changed back to the translucent, water white or light yellow color. When removed from the substantially oxygen free argon environment the dye would then change back to the colored (blue) oxidized state as discussed above.

Example 2

In another example, a dye that was substantially translucent in a substantially oxygen free environment and changed color after exposure to oxygen after a number of hours was formed as follows.

First a stock solution was prepared by dissolving 5 grams of 2-hydroxylmethylcellulose in 95 milliliters of distilled water. The 2-hydroxymethylcellulose had a molecular weight of approximately 90,000 grams per mole. The distilled deionized water was generated from a double reverse osmosis system. The stock solution was stirred vigorously for 30 minutes and then stirred gently overnight. The stock solution was then mixed to eradicate any layer separation.

To prepare the color changeable dye, 0.075 grams ITS having a purity of 85% was mixed with 21.300 grams of the stock solution. 2.50 grams of high molecular weight (400,000-500,000 grams per mole) PDADMA supplied as a 20% solution in deionized water were added to the solution. 3.15 grams of glycerol were also added. The solution was stirred for 5 minutes. Titanium dioxide was ground using a mortar and pestle. The titanium dioxide was ground to greater than 100 nanometer particles. The titanium dioxide was an anatase/rutile mixture and was 99.5% pure. 0.26 grams of the titanium dioxide was added to the solution. 2.30 grams of crushed bentonite (crushed using a mortar and pestle) were then added. The solution was stirred for one minute. The solution was then sonicated for 30 minutes. 0.44 gram of L-ascorbic acid was then added to the solution and mixed for 30 seconds to a minute in the air. At this point the solution was blue/green in color because the ITS was in its oxidized state. 0.35 gram of sodium bisulfate was then added. The solution was mixed under argon for 30 minutes. The solution was spread thin in air and allowed to dry under argon overnight. The ITS was oxidized to the oxidized colored state (blue). This was reversed by exposing the dye to UV light or sunlight while in the substantially oxygen free argon environment. This caused the dye to change back to the translucent, water white, light yellow or yellow orange color.

FIGS. 16-21 show photographs of the color changeable dye described above on the left at approximately 10 minutes, 1 hour 29 minutes, 2 hours 20 minutes, 4 hours 10 minutes, 11 hours 40 minutes and 23 hours of exposure to oxygen respectively. The ink was translucent, water white, light yellow or orange/yellow when dried. After exposure to oxygen, the color change began to occur in the 2-3 hour range. The specific time required is also dependent on the thickness of the film.

Example 3

In another example, a dye that was substantially translucent in a substantially oxygen free environment and changed color after exposure to oxygen after a number of hours was formed as follows.

First a stock solution was prepared by dissolving 5 grams of 2-hydroxylmethylcellulose in 95 milliliters of distilled water. The 2-hydroxymethylcellulose had a molecular weight of approximately 90,000 grams per mole. The distilled deionized water was generated from a double reverse osmosis system. The stock solution was stirred vigorously for 30 minutes and then stirred gently overnight. The stock solution was then mixed to eradicate any layer separation.

To prepare the color changeable dye, 10.000 grams of the stock solution was mixed with 11.5 grams of distilled deionized water. 0.075 gram of ITS having a purity of 85% was then added. 2.50 grams of high molecular weight (400,000-500,000 grams per mole) PDADMA supplied as a 20% solution in deionized water were added to the solution. 2.65 grams of glycerol were also added. The solution was stirred for 5 minutes. Titanium dioxide was ground using a mortar and pestle. The titanium dioxide was ground to greater than 100 nanometer particles. The titanium dioxide was an anatase/rutile mixture and was 99.5% pure. 0.26 grams of the titanium dioxide was added to the solution. 2.30 grams of crushed bentonite (crushed using a mortar and pestle) were then added. The solution was stirred for one minute. The solution was then sonicated for 30 minutes. 0.44 gram of L-ascorbic acid was then added to the solution and mixed for 30 seconds to a minute in the air. At this point the solution was blue/green in color because the ITS was in its oxidized state. 0.35 gram of sodium bisulfate was then added. The solution was mixed under argon for 30 minutes. The solution was spread thin in air and allowed to dry under argon overnight. The ITS was oxidized to the oxidized colored state (blue). This was reversed by exposing the dye to UV light or sunlight while in the substantially oxygen free argon environment. This caused the dye to change back to the translucent, water white, light yellow or yellow orange color.

The ink was translucent, water white, light yellow or orange/yellow when dried. After exposure to oxygen, the color change began to occur in the 2-3 hour range. The specific time required is also dependent on the thickness of the film.

Example 4

In another example, a dye that was substantially translucent in a substantially oxygen free environment and changed color after exposure to oxygen after a number of hours was formed as follows.

First a stock solution was prepared by dissolving 5 grams of 2-hydroxylmethylcellulose in 95 milliliters of distilled water. The 2-hydroxymethylcellulose had a molecular weight of approximately 90,000 grams per mole. The distilled deionized water was generated from a double reverse osmosis system. The stock solution was stirred vigorously for 30 minutes and then stirred gently overnight. The stock solution was then mixed to eradicate any layer separation.

To prepare the color changeable dye, 0.075 grams ITS having a purity of 85% was mixed with 21.300 grams of the stock solution. 2.50 grams of high molecular weight (400,000-500,000 grams per mole) PDADMA supplied as a 20% solution in deionized water were added to the solution. 3.60 grams of glycerol were also added. The solution was stirred for 5 minutes. Titanium dioxide was ground using a mortar and pestle. The titanium dioxide was ground to greater than 100 nanometer particles. The titanium dioxide was an anatase/rutile mixture and was 99.5% pure. 0.26 grams of the titanium dioxide was added to the solution. 2.30 grams of crushed bentonite (crushed using a mortar and pestle) were then added. The solution was stirred for one minute. The solution was then sonicated for 30 minutes. 0.44 gram of L-ascorbic acid was then added to the solution and mixed for 30 seconds to a minute in the air. At this point the solution was blue/green in color because the ITS was in its oxidized state. 0.400 gram of sodium bisulfate was then added. The solution was mixed under argon for 30 minutes. The solution was spread thin in air and allowed to dry under argon overnight. The ITS was oxidized to the oxidized colored state (blue). This was reversed by exposing the dye to UV light or sunlight while in the substantially oxygen free argon environment. This caused the dye to change back to the translucent, water white, light yellow or yellow orange color.

FIGS. 16-21 show photographs of the color changeable dye described above on the right at approximately 10 minutes, 1 hour 29 minutes, 2 hours 20 minutes, 4 hours 10 minutes, 11 hours 40 minutes and 23 hours of exposure to oxygen respectively. The ink was translucent, water white, light yellow or orange/yellow when dried. After exposure to oxygen, the color change began to occur in the 2-3 hour range. The specific time required is also dependent on the thickness of the film.

While the application has been described with reference to certain embodiments, it will be understood by those skilled in the art that various changes may be made and equivalents may be substituted without departing from the scope of the application. In addition, many modifications may be made to adapt a particular situation or material to the teachings of the application without departing from its scope. Therefore, it is intended that the application not be limited to the particular embodiment disclosed, but that the application will include all embodiments falling within the scope of the appended claims.

The invention claimed is:

1. A disposable ophthalmic or medical apparatus comprising:
   a disposable ophthalmic or medical device;
   a color changeable dye composition disposed on the device
   wherein said color changeable dye composition comprises: a redox indicator, a reduction reaction initiator, an electron donor, an oxygen scavenger, and a thickening agent.

2. The apparatus of claim 1 wherein said color changeable dye composition is a first color in the presence of oxygen, capable of changing to a second color upon reduction in a substantially oxygen free environment, and capable of changing back to the first color after exposure to oxygen for a period of time corresponding to the intended use time of said disposable ophthalmic or medical device.

3. The apparatus of claim 1 wherein said ophthalmic or medical apparatus is a contact lens.

4. The apparatus of claim 1 wherein said ophthalmic or medical apparatus is a scalpel.

5. The apparatus of claim 1 wherein said ophthalmic or medical apparatus is a syringe.

6. The apparatus of claim 1 wherein said ophthalmic or medical apparatus is an ophthalmic lens through which a clinician looks to view a patients' eye.

7. The apparatus of claim 1 wherein the color changeable dye composition further comprises an indicator barrier agent.

8. The apparatus of claim 1 wherein the redox indicator is indigo-tetrasulfonate.

9. The apparatus of claim 1 wherein the color changeable dye composition further comprises an agent to facilitate mixing.

10. The apparatus of claim 2 wherein the first color is blue and said second color is translucent or water white.

11. The apparatus of claim 1 wherein the period of time is less than about 60 minutes.

12. The apparatus of claim 1 wherein the period of time is between about 1 and about 168 hours.

13. An apparatus with time controlled color change indication comprising:
a limited use apparatus;
a color changeable dye composition disposed on a portion of the apparatus,
wherein said color changeable dye composition comprises: a redox indicator, a reduction reaction initiator, an electron donor, an oxygen scavenger, and a thickening agent.

14. The apparatus of claim 13 wherein said color changeable dye composition is a first color in the presence of oxygen, capable of changing to a second color upon reduction in a substantially oxygen free environment, and capable of changing back to the first color after exposure to oxygen for a period of time corresponding to a defined time indicating that the apparatus is no longer to be used.

15. The apparatus of claim 13 wherein the color changeable dye composition further comprises an indicator barrier agent.

16. The apparatus of claim 13 wherein the redox indicator is indigo-tetrasulfonate.

17. The apparatus of claim 13 wherein the color changeable dye composition further comprises an agent to facilitate mixing.

18. The apparatus of claim 14 wherein the first color is blue and said second color is translucent or water white.

19. The apparatus of claim 13 wherein the period of time is less than about 60 minutes.

20. The apparatus of claim 13 wherein the period of time is between about 1 and about 168 hours.

\* \* \* \* \*